US009593859B2

(12) United States Patent
Niazi

(10) Patent No.: US 9,593,859 B2
(45) Date of Patent: Mar. 14, 2017

(54) CLEAN ZONE HVAC SYSTEM

(71) Applicant: Sarfaraz K. Niazi, Deerfield, IL (US)

(72) Inventor: Sarfaraz K. Niazi, Deerfield, IL (US)

(*) Notice: Subject to any disclaimer, the term of this patent is extended or adjusted under 35 U.S.C. 154(b) by 0 days.

(21) Appl. No.: 14/717,900

(22) Filed: May 20, 2015

(65) Prior Publication Data

US 2015/0253022 A1    Sep. 10, 2015

Related U.S. Application Data

(63) Continuation of application No. 13/236,523, filed on Sep. 19, 2011, now abandoned.

(51) Int. Cl.
| | |
|---|---|
| *G05D 23/00* | (2006.01) |
| *F24F 7/06* | (2006.01) |
| *C12M 1/00* | (2006.01) |
| *C12M 1/12* | (2006.01) |
| *C12M 3/06* | (2006.01) |
| *C12M 1/34* | (2006.01) |
| *C12Q 3/00* | (2006.01) |

(52) U.S. Cl.
CPC ............ *F24F 7/06* (2013.01); *C12M 23/14* (2013.01); *C12M 25/14* (2013.01); *C12M 27/16* (2013.01); *C12M 29/06* (2013.01); *C12M 41/32* (2013.01); *C12M 47/10* (2013.01); *C12Q 3/00* (2013.01); *Y10T 137/0318* (2015.04)

(58) Field of Classification Search
CPC .................. G05D 23/1934; G05H 23/1931
USPC ........................................ 700/277, 276, 278
See application file for complete search history.

(56) References Cited

U.S. PATENT DOCUMENTS

| | | | |
|---|---|---|---|
| 2010/0070092 A1* | 3/2010 | Winter ...................... | F24F 3/08 700/278 |
| 2010/0163633 A1* | 7/2010 | Barrett ............... | B60H 1/00871 236/49.3 |

* cited by examiner

*Primary Examiner* — Natalia Levkovich
(74) *Attorney, Agent, or Firm* — Sarfaraz K. Niazi

(57) ABSTRACT

A single-pass HVAC systems to isolate zones and to maintain a required clean air quality standard is provided that operates by producing a positive pressure in all zones, while exhausting on a minimal quantity of air required by law. The zones are kept clean by a recirculating fan filter in each zone. The exhaust air is used to exchange heat with incoming air to conserve energy further.

3 Claims, 1 Drawing Sheet

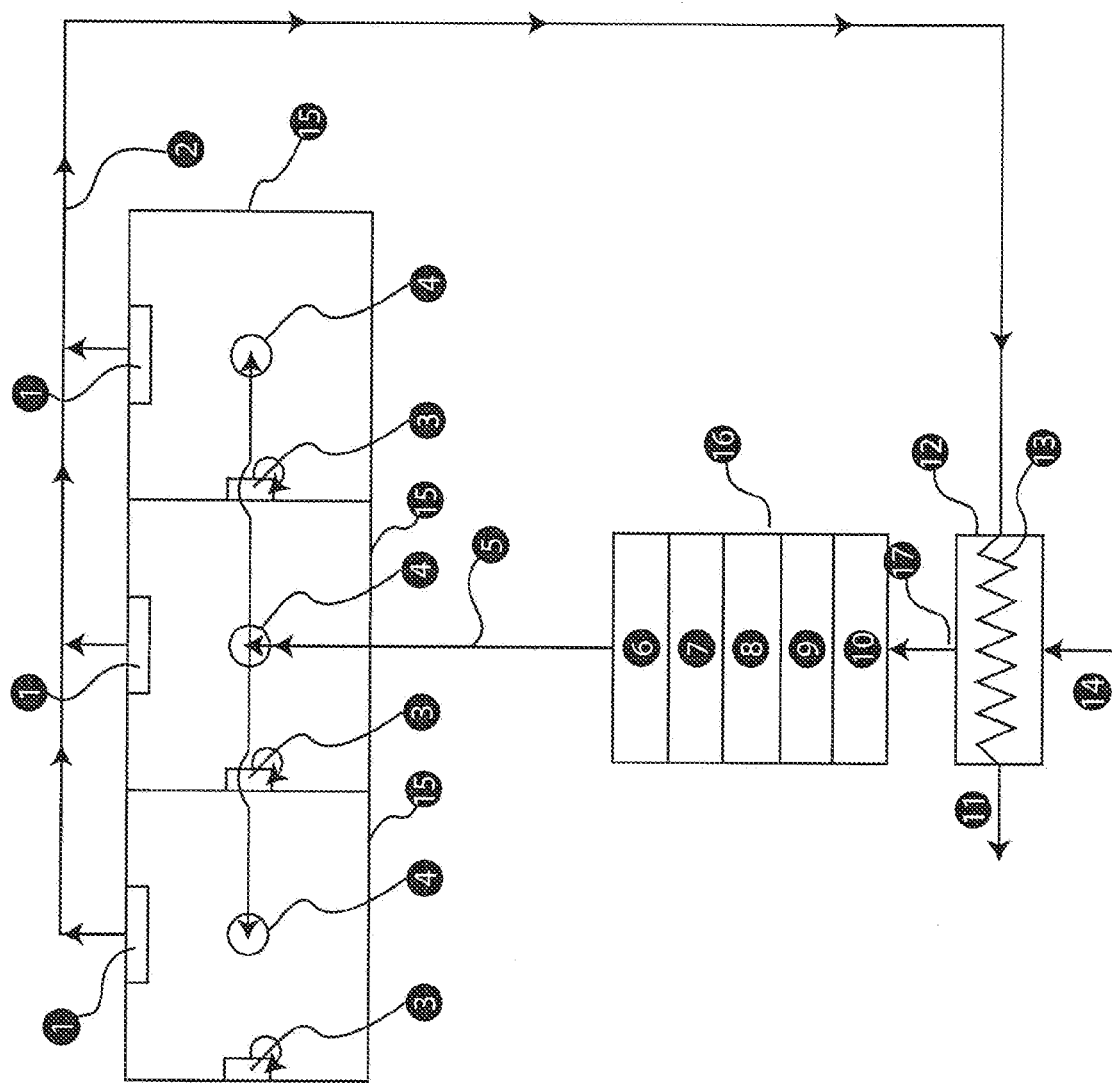

CLEAN ZONE HVAC SYSTEM

CROSS REFERENCE TO RELATED APPLICATION

This application is a continuation of U.S. patent application Ser. No. 13/236,523, entitled "CLEAN ZONE HVAC SYSTEM" filed on Sep. 19, 2011, the contents of which are incorporated herein by reference in its entirety.

BACKGROUND OF THE INVENTION

Various embodiments described herein relate generally to the field of heating, ventilation, and air conditioning (HVAC), and more particularly to HVAC systems able to control different zones independently that locally re-circulate air and receive supply of fresh air from a single air-handling unit.

The exhaust systems within zones remove the air to the outside without recirculation. Such an HVAC system will be particularly useful and effective for use in biological and pharmaceutical manufacturing operations where it is critical to prevent cross contamination between zones, control the quality of air within strict ISO standards and maintain an appropriate temperature despite the heat load from the equipment operating within a zone, all at a reduced cost of installation and operation of a HVAC system.

Additionally, such an HVAC system will be useful for hospitals, research laboratories and other such facilities where a structure demands varying requirements of air quality and isolation from other zones.

A conventional forced air variable air volume (VAV) system distributes air to terminal units installed in habitable spaces throughout a building. The air is cooled or heated central equipment zones. The an supplied is called primary or ventilation air.

The primary air is first tempered through a large air-handling unit and then distributed to the rest of the zones through conventional air ductwork. The large air-handling unit may consist of a supply fan, cooling coil, hearing coil, filters, condensate drain pans, outside air dampers, sensors, controls, etc., but not any return air dampers or controls. Once the primary air leaves the air-handling unit the primary air is distributed throughout the zones through air ductwork and then to in-zone terminal units such as air distribution units and terminal units. A single in-zone terminal unit usually conditions a single space, but some (e.g., a large fan-coil unit) may serve several spaces.

Conventional forced air variable air volume systems work well in various manufacturing operations such as in pharmaceutical and biotechnology manufacturing. In most climates, these VAV systems are typically installed to condition perimeter building spaces and are designed to provide all desired space heating and cooling, outside air ventilation, and simultaneous heating and cooling in different parts of the building during intermediate seasons.

A conventional forced air variable air volume system generally serves also as a recirculating unit wherein the air from the various zones of a building is brought back into the unit to conserve the cost of conditioning the air; this cost can be substantial since it involves humidification or dehumidification, temperature control and air filtration. If the air is supplied to ISO controlled areas where clean air is supplied, recirculation becomes inevitable to conserve cost.

Air recycling has one major disadvantage: it mixes the air from various zones and is the major source of cross contamination between and among the zones. A simple but extremely costly solution is to provide a separate air-handling unit for each zone in need of isolating from other zones. This is how the pharmaceutical and biotechnology industry designs its facilities. The challenges become more formidable in the manufacturing of biological products where each step of manufacturing should be ideally isolated from others as the product progresses to a purer form. An example of this situation arises in the purification of recombinant proteins made from mammalian cells where there remains a risk of viral contamination. Each step of purification reduces the viral load and it is critical that the air from earlier steps should not mix with the air in the zones where later processes are executed. The choice of separate air-handling units resolves the problem but adds substantial capital investment and a very high life-time cost of operations.

To minimize energy consumption, the large air-handling units generally recycle the circulated air and only add a small portion of fresh air. Such recycling, however, may result in air borne contaminants and bacteria, being spread throughout the building resulting in "sick building syndrome." Other disadvantages may include draughts, lack of individual control, increased building height required to accommodate ducting, and noise associated with air velocity. Additionally, for many buildings, the use of in-zone terminal units may be limited to perimeter spaces, with separate systems required for other areas. More controls may be needed as compared to other systems.

In many systems, the primary air is supplied at a constant rate with no provision for shut off, which may be a disadvantage as tenants may prefer to shut off their heating or air conditioning or management may desire to do so to reduce energy consumption. In many systems, low primary chilled water temperature and or deep chilled water coils are required to control space humidity accurately, which may result in more energy consumption from a chiller, cooling tower, and/or pumps. A conventional forced air variable air volume system may not be appropriate for spaces with large exhaust requirements such as labs unless supplementary ventilation is provided. In many systems, low primary air temperatures require heavily insulated ducts. In many systems, the energy consumption is high because of the power needed to deliver primary air against the pressure drop of the terminal units. The initial cost for a VAV system may be high. In many systems, the primary air is cooled, distributed, and may be subsequently re-heated after delivery to a local zone, thus wasting energy. In many systems, individual zone control is expensive as an individual terminal unit or fan coil unit is required for each zone, which may be costly to install and maintain, including for ancillary components such as controls. Moving large flow rates of air thru ductwork is inefficient and wastes energy. Mold and biocides may form in the ductwork and then be blown into the ambient/occupied space.

There remains a need to provide an HVAC system that is capable of providing a low cost solution, both in its design and operation while maintaining a complete isolation of zones and also making it possible to provide a different class of air in each zone; the ideal invention will also allow a separate temperature in each zone and requires very low maintenance.

The present invention discloses a single-pass HVAC systems to isolate zones and to maintain a required clean air quality standard is provided that operates by producing a positive pressure in all zones, while exhausting on a minimal quantity of air required by law. The zones are kept clean by a recirculating fan filter in each zone. The exhaust air is used to exchange heat with incoming air to conserve energy further.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

The present disclosure generally provides heating, ventilation, and air conditioning (HVAC) systems, components, and control systems. In many embodiments, an HVAC system includes distributed zone control units that locally re-circulate air to zones serviced by each respective zone control unit. A zone control unit can condition the re-circulated air by adding heat, removing heat, and/or filtering.

In many embodiments, an HVAC system includes an exhaust air system that extracts air from each of the HVAC zones and discharges the extracted air as exhaust air. In many embodiments, an HVAC system includes a heat recovery radiator for exchanging heat between the incoming outside intake air and the outgoing exhaust air. In many embodiments, an HVAC system includes one or more filters and/or a humidity adjustment device for conditioning the supply airflow prior to distribution to the distributed HVAC zone control units. In many embodiments, the distributed HVAC zone control units include control electronics having an Internet protocol address and can include a resident processor and memory providing local control functionality. In many embodiments, the zones are kept separate by creating a positive pressure in them by adjusting the flow of supply air and the rate of exhaust. In many embodiments, the ISO quality of air in each zone is maintained by recirculating air within the room through HEPA filters and also the temperature is individually adjusted in each zone by activating the heating and cooling systems provided in each zone.

The disclosed HVAC systems, zone control units, and control systems provide a number of advantages. These advantages may include reduced installed system cost; improved air quality; increased Leadership in Energy and Environmental Design (LEED) points; improved quality; reduced maintenance costs; improved maintainability; reduced sound; reduced energy usage; improved control system; improved building flexibility; superior Indoor Air Quality (IAQ); exceeding American Society of Heating, Refrigerating and Air-Conditioning Engineers (ASHRAE) standards; flexible application in a variety of different types of buildings/applications; and/or reduced manufacturing costs and installed cost.

BRIEF DESCRIPTION OF DRAWINGS

FIG. 1 describes a general layout of the HVAC system showing a common air-handling unit, exhaust and recirculation systems in the zones and a flow chart for the movement of air through a heat exchanger.

DETAILED DESCRIPTION OF THE INVENTION

The HVAC systems used in various industries that require isolation of zones and providing clean air in the zones are the most expensive components of facility operations, often costing as much as 20-30% of the total cost of construction and adding a very large operation cost since most of these units are run continuously to maintain a specific ISO class of clean room. Industries that would include this type of requirements are pharmaceutical manufacturing, biotechnology manufacturing, surgical rooms, health care patient facilities, electronic manufacturing operations and variety of other industries where air particulate count is strictly controlled. The ISO 14664 provides a classification of clean rooms wherein not only is the particle count specified but also the size of particles; larger particles are more likely to bring biological contaminants that may be undesirable and in some instances even small particles can ruin a manufacturing process such as in electronic industry. It is for this reason that a continuously recirculating air-handling systems are used as the cost of producing such higher quality air. The use of a single-pass system would increase the cost of operations substantially.

The present invention provides a single-pass system with very low capital and maintenance cost; instead of recirculating air through a common air-handling unit, each zone has its own air-recirculation unit that performs the cleaning of the air in the zone. This approach also allows maintenance of a different ISO class air in each zone without affecting the quality of neighboring zones. The hardware maintenance is also low since the HEPA filters provided are of smaller sizes in each zone compared to large filters needed for central recirculation systems. The recirculation unit in each zone obviates the need to bring a larger volume of air as may be required to achieve a specific number of air-exchanges to clean the zone; this significant component of invention allows use of small size air-handling systems as the sole purpose of the air-handling units is to provide the replacement fresh air that is required according to local building codes such as ASHRAE 62-2004 code. In most of industrial operations this would translate into providing at least 0.12 $CFM/ft^2$ The method of isolating a plurality of zones and maintaining a pre-determined ISO quality of air and temperature according to claim 1, wherein the fresh air supplied by the first air handling unit is 0.12 $CFM/ft^2$ of fresh air. So, for a 100,000 square foot clean zone facility, the air-handler will be capable of providing about 12,000 CFM. Assuming the temperature of inlet air is 90 F and the supply air is at 40 F, the energy required is about 120 Kw/hr or costing about $1.20 per hour to run a 12,000 CFM unit. This should be compared with a single-pass system where the total volume of air in 100,000 sq-ft facility will be a million CFM requirement needing a 85 times larger air-handling system with more than 100 times the cost since it will require much larger ducting and other control systems. This calculation is based on about 60 exchanges per minute for clean rooms; for lesser exchanges, such as 30, the size will be proportionally smaller, yet still it will be several times the air handling unit required in the present invention. It is further noteworthy that heating or cooling at the point of use such as in each zone compared to a central heating and cooling system is more efficient as the losses of energy in the distribution of air are minimized.

The zones are isolated in the present invention by maintaining a positive pressure of at least 0.05 inch water gauge in all zones; this assures that no air will enter the zones from outside and the only source of air will be the supply air; this pressure is readily maintained by adjusting the flow of supply air and the exhaust and this can be done automatically by installing pressure sensors in the zone that would govern the damper opening of the inlet and the outlet to adjust the pressure continuously.

The temperature in the zones is maintained by two means; first, the supply air is kept at a low temperature, generally 10 C below the lowest temperature of any zone; however, it may not be enough to maintain a required temperature as the activity in the zone would largely determine the heat output and the temperature in the zone. It is for this reason, local heating and cooling of supply air is provided through the recirculating units. This will also allow maintaining different temperatures in different zones as specific work might require. An excellent example of this will be the manufacturing of recombinant proteins where some steps require a much lower temperature such refolding or downstream purification to reduce loss of proteins. The present invention will provide any temperature to any zone and compensate for any amount of heat generated within a zone without affecting other zones.

The air cleanliness in the zones is of great importance in many sensitive operations both biological and electronic. The class of air such as class 10,000 is used in downstream purification and class 100,000 for upstream manufacturing of recombinant proteins. It is not possible using existing designs to provide two different kinds of clean air using the same air-handling unit. The present invention solves this problem by disposing air-recirculating units fitted with HEPA filters within the zone. How fast these units operate will determine the number of air exchanges and that is the critical parameter for maintaining a certain class of cleanliness.

While the air exhausted is much smaller in the present invention compared to traditional systems, the exhaust air nevertheless has energy that can be of use; in hot climates, this would cool down the incoming air and in cold climates it can heat the air before it enters the air-handling unit. This is achieved by passing the exhaust air is passed through a radiator over which the fresh air passes before entering the air-handling unit; no contact between the two airflows is allowed, so the purpose of this component of invention is to conserve heat energy. This further reduces the cost of operations.

Now referring to the drawing, the FIG. 1 shows a preferred embodiment of the HVAC system of the present invention. The system comprises a air-handling unit 16, which further comprises means of filtration 10, a means of dehumidification 9, a means of humidification 8, a means of cooling 7 and a means of heating 6 and other associated standard features like blowers, dampers and control mechanisms. The source of air for the air-handling unit 16 comes from a fresh air inlet 14 into a plenum 12, where resides a radiator 13 and an outlet for air 17 that has undergone heat exchange with exhaust air 2, which is then finally exhausted as outside vent 11 after exchanging heat with fresh air 14. Upon reaching the air-handling unit 16, the air intake 17 undergoes a process of conditioning before being brought as supply air 5 to vents 4 in the zones 15. The supply air vents are preferentially located in the ceiling of the zones and have a design to disperse air throughout the zone 15. For larger zones, a plurality of vents 4 can be disposed to in each zone.

Each zone 15 is further disposed with at least one exhaust system 1 that generally comprises fans, dampers and control mechanisms to remove supply air as exhaust air 2, which then feeds the radiator 13 and then exhausted through an outside vent 11. The exhaust units are preferably located at a low level in the wall of the zones or in the floor.

The claimed HVAC system further comprises at least one air-recirculating unit 3 disposed in each zone and generally comprising a fan, a HEPA filter, a sealed housing and a control mechanism; the air-recirculating unit 3 is capable of circulating sufficient volume of air to comply with the requirements to clean the supply air in the zones 15 to a pre-determined ISO class. Given below are the air changes that the air-recirculating unit will be capable of meeting the ISO 14644 standards:

Class 1: 540 to 600+ air changes per hour
Class 10: 540 to 600 air changes per hour
Class 100: 400 to 480 air changes per hour
Class 1,000: 120 to 150 air changes per hour
Class 10,000: 45 to 60 air changes per hour
Class 100,000: 20 to 30 air changes per hour Clean room designs also often mandate a percentage ceiling coverage of the supply of recirculated air; where such compliance is required, the air-recirculation unit may be further comprise a system of ducts and supply of recirculated air.

Other variations are within the spirit of the present invention. Thus, while the invention is susceptible to various modifications and alternative constructions, certain illustrated embodiments thereof are shown in the drawing and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

In the following description, various embodiments of the present invention will be described. For purposes of explanation, specific configurations and details are set forth in order to provide a thorough understanding of the embodiments. The present invention can, however, be practiced without the specific details. Furthermore, well-known features may be omitted or simplified in order not to obscure the embodiment being described.

In a first embodiment, the HVAC system of the present invention is single pass HVAC system that provides only the minimal quantity of fresh air required by law.

In a second embodiment, the HVAC system of the present invention is used to isolate the air between various zones of a building, preventing cross-contamination.

In a third embodiment, the HVAC system of the present invention is used to clean air in the zones to specific ISO class for sensitive operations including manufacturing of drugs and electronic parts.

In a fourth embodiment, the HVAC system of the present invention is capable of maintaining different temperatures in each zone of a building.

In a fifth embodiment, the HVAC system of the present invention is capable of maintaining a different ISO Class of air in each zone.

In a sixth embodiment, the HVAC system of the present invention is capable of conserving energy by exchanging heat between the exhaust air and the incoming fresh air.

In a seventh embodiment, the HVAC system of the present invention is useful in the manufacturing of biological drugs wherein each step of purification requires total isolation from other zones.

In an eight embodiment, the HVAC system of the present invention is useful in protecting patients in a hospital from infectious organisms in other patient rooms preventing hospital acquired infections, one of the largest single cost of healthcare.

In a ninth embodiment, the HVAC system of the present invention is useful in establishing safe surgical rooms.

In a tenth embodiment, the HVAC system of the present invention is inexpensive to install and run.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A single-pass system for independently controlling the environment in a plurality of building zones comprising:
    a central air-handling unit for supplying fresh air comprising:
    a heat exchanger including a plenum with a fresh air inlet in fluid communication with outside fresh air;
    a fresh air outlet;
    the plenum having a radiator with an exhaust air inlet and an exhaust air outlet;
    an air handling unit having means of filtering, means of heating, means of cooling, means of humidifying and means of dehumidifying the fresh air, the air-handling unit being in fluid communication with the fresh air outlet of the heat-exchanger;
    a plurality of ducts to supply fresh air independently from the air-handling unit to each building zone;
    a plurality of exhaust units disposed in each zone and each comprising a fan, a damper and a control mechanism to continuously or periodically exhaust remove a volume of air from each building zone;
    a means of extracting thermal energy from the exhaust air comprising a common duct connecting each of the exhaust air units in parallel to the exhaust air inlet of the radiator of the heat-exchanger and allowing the exhaust air to vent.

2. The single-pass system of claim 1, wherein each building zone additionally comprises a secondary air-handling unit capable of filtering, heating, cooling, adjusting humidity and recirculating air independently in each building zone.

3. The single-pass system of claim 1 for independently controlling the environment in a plurality of building zones, wherein the plurality of building zones is a contamination-sensitive zone in pharmaceutical manufacturing, biotechnology manufacturing, surgical rooms healthcare patient facilities, electronic manufacturing operations and a variety of other industries where air particulate count is strictly controlled.

* * * * *